United States Patent [19]

Herrmann et al.

[11] Patent Number: 5,425,267

[45] Date of Patent: Jun. 20, 1995

[54] CORROSION SIMULATOR AND METHOD FOR SIMULATING CORROSION ACTIVITY OF A PROCESS STREAM

[75] Inventors: William B. Herrmann, Sugarland, Tex.; Daniel Mull, Lockport, Ill.; John G. Hyatt, Sugarland, Tex.; Paul Fearnside, Sugarland, Tex.; Russell C. Strong, Richmond, Tex.

[73] Assignee: Nalco Chemical Company, Naperville, Ill.

[21] Appl. No.: 114,479

[22] Filed: Aug. 31, 1993

[51] Int. Cl.⁶ .......................................... G01N 17/00
[52] U.S. Cl. .......................................... 73/86; 422/53; 73/863.12; 436/6
[58] Field of Search ................ 73/86, 863.12; 422/53; 436/6; 203/7; 138/DIG. 6

[56] References Cited

U.S. PATENT DOCUMENTS

| | | | |
|---|---|---|---|
| 2,532,257 | 11/1950 | Kirshenbaum et al. | 422/53 |
| 2,664,744 | 1/1954 | Bilhartz et al. | |
| 3,649,167 | 3/1972 | Sawyer | 73/863.12 |
| 3,960,496 | 6/1976 | Schieber | 422/53 |
| 4,056,968 | 11/1977 | Winslow, Jr. | 73/19.07 |
| 4,065,373 | 12/1977 | Martin et al. | |
| 4,335,072 | 6/1982 | Barnett et al. | 422/53 |
| 4,416,996 | 11/1983 | von Klock et al. | 436/6 |
| 4,488,939 | 12/1984 | Fu | 204/153.11 |
| 4,599,217 | 7/1986 | Winston et al. | 422/53 |
| 4,683,035 | 7/1987 | Hunt et al. | |
| 4,711,131 | 8/1987 | Hopkins | 73/799 |
| 4,754,698 | 7/1988 | Naish | 99/275 |

FOREIGN PATENT DOCUMENTS

| | | | |
|---|---|---|---|
| 2317530 | 11/1973 | Germany | 422/53 |
| 1275905 | 6/1972 | United Kingdom | 73/863.12 |

OTHER PUBLICATIONS

A. Wachter and R. S. Treseder; Corrosion Testing; Evaluation of Metals for Process Equipment; Shell Development Company, Emeryville, Calif.; Jun. 1947.

*Primary Examiner*—Hezron E. Williams
*Assistant Examiner*—Daniel S. Larkin
*Attorney, Agent, or Firm*—Robert A. Miller; James J. Drake

[57] ABSTRACT

Apparatus for simulating corrosion activity of a process stream on equipment and transport lines. The apparatus includes a series of modular canisters coupled to a process stream source and a process stream discharge point. A cooling coil is positioned within each canister and the cooling coils are interconnected in series. The first cooling coil is coupled to a coolant source and the last cooling coil is connected to a coolant discharge. The process stream flows thorough the series of canisters and the coolant flows through the coils in counterflow to the process stream to cool and partially condense the process stream. Corrosion activity and temperature within the canister are monitored using corrosion probes and/or coupons. Modular construction of the canisters permits disassembly and reassembly to adapt the simulator to different simulation applications.

14 Claims, 3 Drawing Sheets

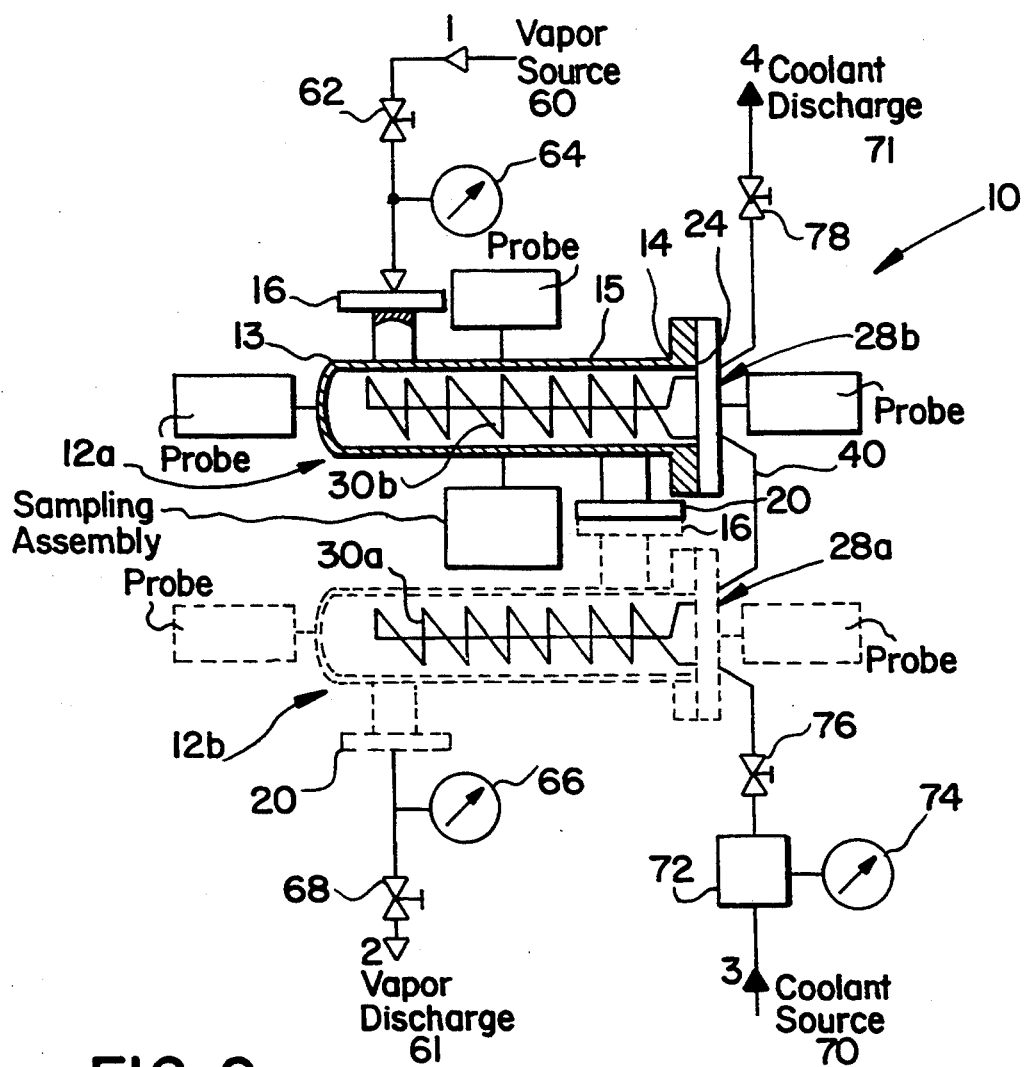
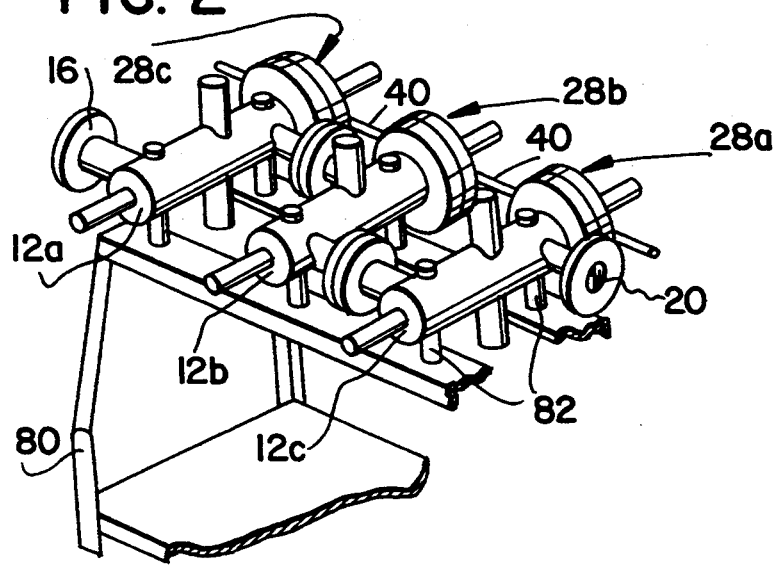

CORROSION SIMULATOR AND METHOD FOR SIMULATING CORROSION ACTIVITY OF A PROCESS STREAM

BACKGROUND OF THE INVENTION

1. FIELD OF THE INVENTION

The present invention relates generally to an apparatus and method for simulating corrosion activity and, more particularly, to an apparatus and method for simulating corrosion activity of process streams on process machinery.

2. DESCRIPTION OF RELATED ART

Corrosion in industrial and process installations is a major and continuous problem, particularly in chemical plants and petroleum refineries. Corrosion activity occurs within process machinery and transport lines to varying degrees depending upon such factors as the corrosivity of the process stream and its condensates, the temperature of the process, process velocities, and the metallurgy of the equipment employed in the process. Such corrosion activity can adversely affect the performance of process equipment, reduce the useful life of equipment and lines, and necessitate costly maintenance, repair and replacement of system components. Consequently, corrosion reduction, or at least the mitigation of the effects of corrosion, is a continuing concern in industry.

The establishment of an effective corrosion control program in a particular industrial installation begins with information on the corrosion activity expected or actually occurring within the installation machinery. Such information typically relates to the source of the corrosion taking place, the location of the corrosion activity, the type and rate of the corrosion activity, and the process parameters affecting corrosion initiation and propagation. One important source of corrosion is process vapors and their condensates. Many process vapor streams contain corrosive components that initiate corrosion upon condensation. Aqueous condensation leads to much of this corrosion activity and occurs primarily in heat exchange units and transport lines. The effects of such corrosion can be mitigated through the implementation of a corrosion control program that may include the use of corrosion inhibiting chemicals. However, the design, implementation, and optimization of such a program usually requires information on the corrosion activity itself.

A number of methods are known for collecting information on the nature of corrosion activity caused by process vapors and vapor condensates and on the process parameters affecting the initiation and propagation of corrosion. It is known, for instance, to insert corrosion probes into a process stream by mounting the probes directly in the process machinery or lines. While this method may supply information on corrosion activity actually occurring at the precise point of insertion, the probe placement will rarely correspond to the actual point of the worst corrosion activity, which often changes over time depending upon variations in process parameters. In addition, direct placement of corrosion probes in process equipment generally does not provide a profile of corrosion activity as a function of temperature and aqueous condensation.

Another method for determining corrosion activity of process vapors and condensates is simulation. As used in the present context, simulation refers to physical testing and analysis. In known corrosion simulators, a slip stream of process vapor is diverted and passed through a simulator circuit consisting in a prepiped bank of condensing areas or chambers. Water cools the vapor stream and causes aqueous condensation within the simulator. Corrosion probes, weight loss coupons, and condensate samples are then used to evaluate the location, type, and rate of corrosion taking place in the simulator. This corrosion activity is then related to the corrosion actually occurring or expected in the actual process machinery from which the slip stream was taken.

In one existing corrosion simulator a slip stream of vapors is circulated through a cooling coil positioned in a water box. Cooling water circulated through the water box in counterflow to the vapor stream causes aqueous condensation within the cooling coil. Corrosion and temperature probes detect corrosion activity occurring within the cooling coil. While this arrangement does provide information on corrosion activity and can establish a corrosion profile related to temperature, it is susceptible to operational difficulties, particularly the maintenance of the desired cooling water level and flow within the water box. In addition, the prepiped arrangement of the cooling coil and water box limit the adaptability of the simulator to a particular simulation application.

In another known apparatus for simulating corrosion activity, process vapor is circulated through a prepiped bank of condensers including a primary condenser and several smaller condensers. Cooling coils located in each of the condensers cause aqueous condensation of the vapor stream to simulate conditions in heat exchange units. The cooling coils am piped in parallel and take flow of cooling water from a header. The cooling water flow through each of the cooling coils is controlled independently to cause condensation at desired locations in the simulator and to generate a corrosion profile. Temperature and corrosion probes positioned in the condensers monitor corrosion activity and temperature. However, this simulator has a number of drawbacks. The various flow rates of cooling water through each cooling coil are difficult to control and coordinate, making a clear corrosion profile difficult to obtain. In addition, the prepiped arrangement of the simulator does not provide the flexibility needed to adapt the simulator to different simulation conditions and applications.

The present invention is directed to overcoming or minimizing the drawbacks of the existing techniques set forth above.

SUMMARY OF THE INVENTION

In accordance with one aspect of the invention, there is provided a corrosion simulator including a plurality of canisters each having an inlet for receiving a process stream and an outlet for discharging the process stream. Each canister is also provided with at least one probe port. The canisters are interconnected in series with the first canister in the series coupled to a process stream source and the outlet of the last canister being coupled to a process stream discharge point. The simulator further includes a plurality of cooling coils with one cooling coil being positioned within each of the canisters. Each of the cooling coils is provided with an inlet for receiving a coolant stream and an outlet for discharging the coolant stream. The cooling coils are interconnected in series with a first coil being positioned within the last canister and the inlet of the first coil in the series being coupled to a source of coolant. A last cooling coil in the series of coils is positioned within the first canister, with the outlet of the last coil being coupled to a coolant discharge point.

In accordance with another aspect of the present invention, there is provided a corrosion simulator that includes a canister having an inlet coupled to a process line for diverting a portion of the process stream flowing through the line into the canister, an outlet coupled to the process line downstream from the inlet for discharging the portion of the process stream, and at least one probe port. The simulator also includes a cooling coil positioned within the canister. The cooling coil has an inlet coupled to a source of coolant for receiving a stream of coolant into the cooling coil, and an outlet for discharging the coolant stream. The simulator further includes a probe removably positioned within one of the probe ports, and a corrosion detecting probe or coupon mounted adjacent to the cooling coil within the canister for balancing the flow of the process stream through the canister.

In accordance with a further aspect of the present invention, there is provided a method for simulating the corrosion activity of a process stream. The method includes the steps of passing the process stream through a series of canisters, passing coolant through a series of cooling coils in counterflow to the process stream, condensing at least a portion of the process stream within the series of canisters, and monitoring the corrosion activity within the canisters.

BRIEF DESCRIPTION OF THE DRAWINGS

The present invention will become more fully understood from the following detailed description, taken in conjunction with the accompanying drawings, wherein like reference numerals refer to like parts, in which:

FIG. 1 is a diagrammatic view of a corrosion simulator in accordance with the invention illustrating the flow of a process stream and a coolant stream through certain of the elements included in a typical installation of the corrosion simulator;

FIG. 2 is a perspective view of a series of modular canisters in accordance with the invention, mounted on a supporting rack;

Figure 3:
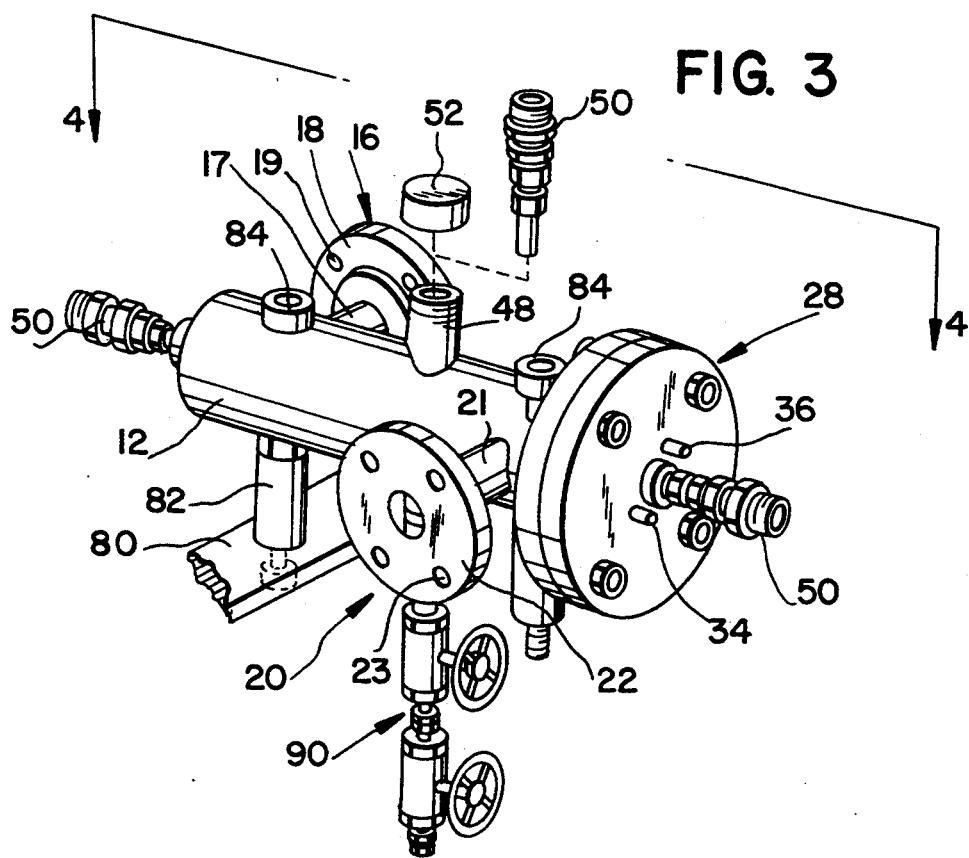
FIG. 3 is a perspective view of a single canister according to the invention illustrating the location of the inlet, the outlet, the cooling coil assembly, and several probes.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the appended claims.

DESCRIPTION OF THE PREFERRED EMBODIMENTS

Turning now to the drawings and referring to FIG. 1, a corrosion simulator is diagrammatically illustrated along with certain of the components included in a typical installation. The corrosion simulator, designated generally by the reference numeral 10, preferably comprises a plurality of canisters 12a,12b, 12c coupled in series. Although the simulator 10 as illustrated in FIGS. 1 and 2 includes only two and three canisters, the number of canisters actually utilized in a particular simulation application will vary depending upon the simulation requirements, and a typical simulation may require a single canister or seven or more canisters coupled in series. Throughout the following discussion, reference will generally be made only to canister 12 and its parts. However, it should be understood that all canisters 12a,12b, 12c in the series of canisters described are substantially similar and contain identical parts, unless indicated otherwise.

As shown in FIG. 1, and as will be more fully discussed below, the canister 12 is preferably cylindrical in shape, having a blind first end 13, a second end 14 comprising a cooling coil port 24, and a lateral wall 15. The canister 12 further comprises an inlet 16 for receiving a process stream and an outlet 20 for discharging the process stream. As depicted in FIG. 1, the inlet 16 is located in the lateral wall 15 adjacent the first end 13, and the outlet 20 is located in the lateral wall 15 adjacent the second end 14. This arrangement of the inlet and outlet causes the process stream entering the inlet 16 to circulate through the canister 12 before exiting through the outlet 20. As will become apparent in the following discussion, because the canister 12 is of a modular construction, the port designated as the inlet 16 in the present description can alternatively serve as the outlet 20 and vice versa, simply by inverting the modular canister 12. This design offers the significant advantage of facilitating the coupling of a plurality of canisters 12a,12b, 12c in series, with the inlet 16 of one canister 12b taking flow from the outlet 20 of the canister 12a immediately preceding it in the series.

When a series of canisters is installed for a particular simulation, the inlet 16 of the first canister 12a in the series of canisters is coupled to a process stream source 60 and the outlet 20 of the last canister 12b in the series of canisters is coupled to a process stream discharge 61. In a typical plant installation, the process stream source 60 will be a tap line diverting a slip stream from process machinery or a transport line. The process stream discharge 61 will typically be a return line connected to a point in the process machinery downstream from the tap line from which the source 60 originates. In operation, when a sufficient pressure drop is established between the process stream source 60 and the process stream discharge 61, the process stream flows from the source 60 and through the series of canisters 12a,12b, 12c to the discharge 61.

The canister 12 should be made of a material of sufficient mechanical strength to withstand the pressures and temperatures likely to arise in the simulation intended. In addition, at least those portions of the canister wetted by the process stream should be sufficiently resistant to corrosion to ensure the canister a reasonably long useful life. The canister 12 may typically be made of carbon steel.

Figure 5:
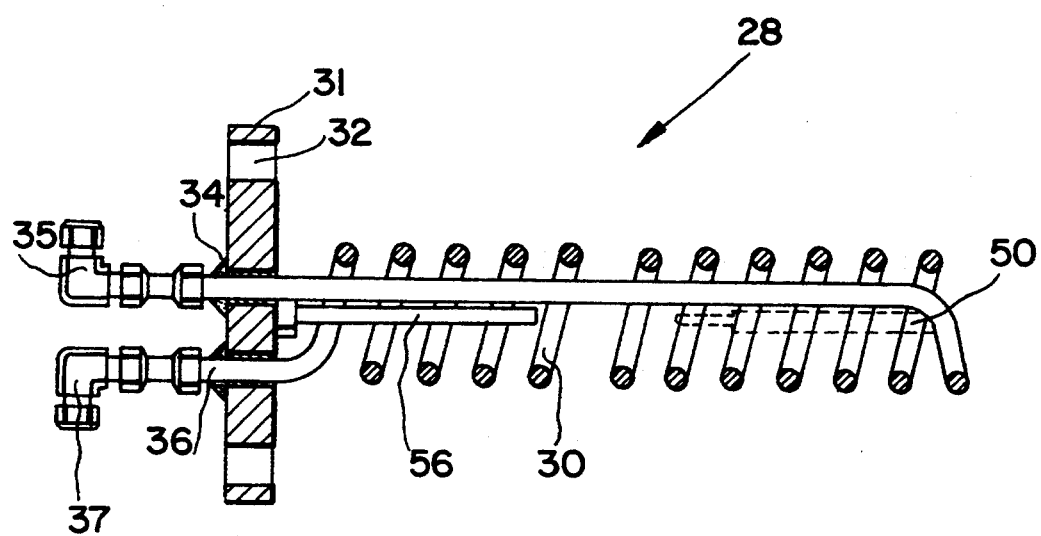
FIG. 5 is a partial sectional view of a cooling coil assembly according to the invention.

A cooling coil 30 is removably positioned within the canister 12 through the cooling coil port 24. In the preferred embodiment, the cooling coil 30 is pan of a cooling coil assembly, generally designated by the reference numeral 28 in the drawings. As will be more fully described below in reference to FIG. 5, the cooling coil assembly 28 includes a cooling coil 30, a coolant inlet 34, a coolant outlet 36, and a coil mounting flange 31. The coil assembly 28 may advantageously include a probe 50 or corrosion coupon 56, as shown in FIG. 5.

As can be seen diagrammatically in FIG. 1, where several canisters 12a, 12b are coupled in series, each canister 12a, 12b is mated with a respective cooling coil 30a, 30b. Tubing 40 connects the outlet 36 of the first coil 30a in the series of coils to the inlet 34 of the successive coil 30b. When installed, the inlet of the first coil in the series of coils is coupled to a coolant source 70 and the outlet of the last coil in the series of coils is coupled to a coolant discharge 71. In a typical plant installation, the coolant source 70 will be a cooling water supply line located near the deck where the simulator 10 is placed. The coolant discharge 71 will typically be a drain line connected to a sewer. In operation, when a sufficient pressure drop is established between the coolant source 70 and the coolant discharge 71, coolant flows from the coolant source 70 and through the series of cooling coils 30a, 30b to the coolant discharge 71. The use of a refrigerated cooling system, such as a glycol-based system, may advantageously be used in the place of a water-based system where additional cooling is required in a particular simulation.

The cooling coil 30 may be made of any suitable tubing material having good mechanical strength, sufficient resistance to corrosion, and adequate thermal conductivity. A number of suitable materials are well known in the field of heat exchanger design, with materials such as admiralty brass or carbon steel being typical, unless a specific simulation requires otherwise as discussed below. The material selected for the cooling coil 30 must also be capable of bending to the radius required for insertion into the canister 12 if the coil is formed by bending a tubular stock into the coil described. Because much of the condensation initiates on the surface of the cooling coil 30 during operation of the simulator 10, in certain applications it may be desirable to consider the cooling coil 30 a corrosion coupon from which corrosion data may be determined. In such cases, the cooling coil may be constructed of any material that will provide an indication of the corrosion activity present in the plant machinery or lines. Where the cooling coil 30 is used to gather corrosion data, it is useful both as a weight loss coupon and for analysis of the surface effects of corrosion on condensing surfaces.

As indicated in FIG. 1 by the arrows 1, 2, 3, 4 representing the process stream source 60, the process stream discharge 61, the coolant source 70, and the coolant discharge 71, in operation, the process stream flowing from the process stream source 60 passes through the canister 12 or series of canisters 12a, 12b in counterflow to the coolant stream flowing from the coolant source 70 passing through the coil 30 or series of coils 30a, 30b. When a number of canisters are interconnected in series, with respect to the direction of flow, the first canister 12a in the series of canisters houses the last coil 30b in the series of coils, with the last canister 12b in the series of canisters housing the first coil 30a. In this preferred embodiment, the hottest portion of the process stream, entering the first canister 12a in the series of canisters, is cooled by the warmest coolant flowing through the last coil 30b in the series of coils. The coolest portion of the process stream flowing through the last canister 12b in the series is then cooled by the lowest temperature coolant incoming from the coolant source 70. The countercurrent flow relation between the process stream and the coolant stream is preferred because this counterflow arrangement most closely stimulates corrosion activity occurring in process machinery and transport lines.

As indicated in FIG. 1, in a typical installation the simulator 10 includes an upstream process stream block valve 62 between the process stream source 60 and the inlet 16. A pressure gauge 64 is advantageously connected between the upstream process stream block valve 62 and the inlet 16. Similarly, a pressure gauge 66 and a downstream process stream block valve 68 are connected between the outlet 20 of the last canister 12b in the series of canisters and the process stream discharge 61. This arrangement permits isolation of the simulator 10 from the process stream source 60 and discharge 61 for installation and subsequent servicing of the simulator. The pressure gauges 64 and 66 provide information on incoming and outgoing pressures of the process stream flowing through the simulator 10 and aid in troubleshooting should process stream flow diminish.

Between the coolant source 70 and the first coil 30a, housed, as indicated above in the last canister in the series of canisters 12b, there is advantageously provided an adjustable pressure regulating valve 72 with a pressure gauge 74. In many plant installations cooling water pressure may vary widely, and the pressure regulating valve 72 may be set to maintain a constant incoming coolant pressure and thus to stabilize the flow rate of the coolant stream through the simulator 10. An upstream coolant block valve 76 is preferably provided between the coolant source 70 and the inlet to the first coil 30a in the series of coils, and a similar downstream block valve 78 is provided between the outlet of the last coil 30b in the series of coils and the coolant discharge 71. The upstream and downstream coolant block valves 76 and 78 facilitate installation and subsequent servicing of the simulator 10.

In a typical installation, the corrosion simulator 10 includes several modular canisters 12a, 12b, 12c coupled in series and mounted on a supporting rack 80 as depicted in FIG. 2. The supporting rack 80 may be situated at any convenient location, but it is preferably located at an equipment level near the process stream source 60 and the process stream discharge 61. Support risers 82 are provided for rigidly mounting the canisters 12a, 12b, 12c on the supporting rack 80. As is more clearly depicted in FIGS. 3 and 4, mounting nuts 84 are preferably welded onto the external surface of the lateral wall 15 in order to facilitate mounting of the canisters 12a, 12b, 12c on the support risers 82. These mounting nuts 84 are preferably provided on both the upper and lower surfaces of the lateral wall 15, as shown in FIG. 4. This arrangement offers the advantage of allowing the modular canister 12 to be inverted for mounting. This feature is particularly useful where a number of canisters are to be coupled in series and the entire series mounted on a supporting rack 80 as shown in FIG. 2.

Figure 4:
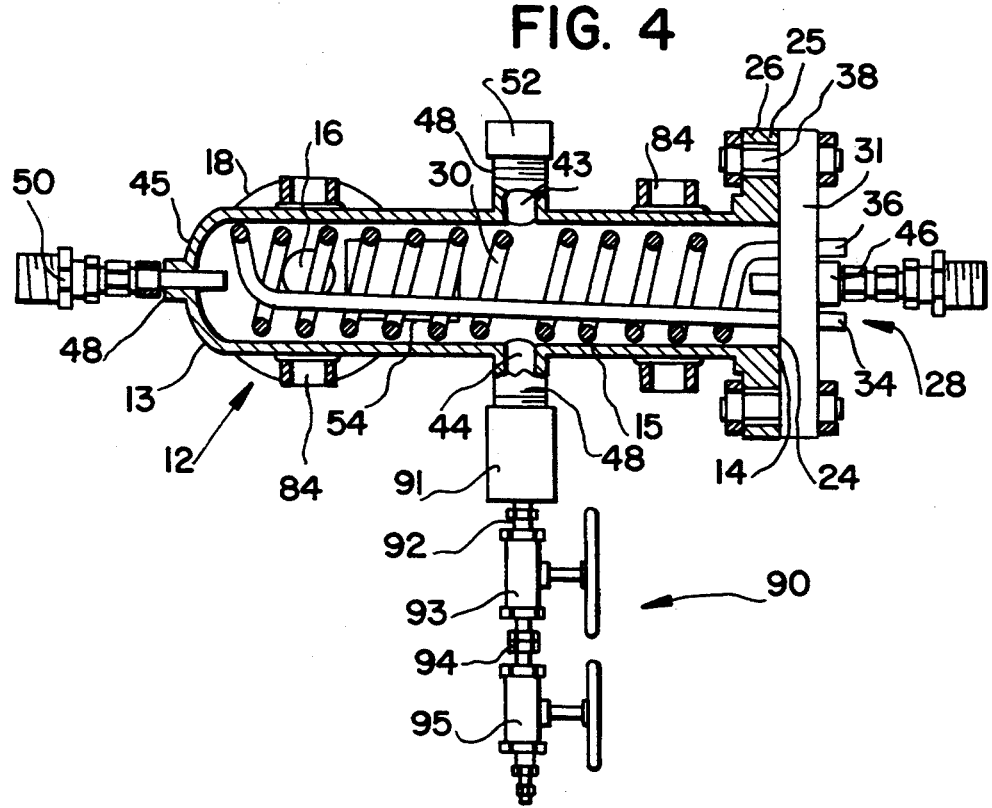
FIG. 4 is a partial sectional view of the canister substantially along line 4—4 of FIG. 3 showing the placement of the cooling coil within the canister as well as a sampling assembly according to the invention.

Turning more specifically now to the preferred embodiment of the canister 12 and coil assembly 28, along with their related hardware, FIG. 3 shows a perspective view of a typical canister 12 on which a coil assembly 28 has been removably positioned. As illustrated in FIGS.

3 and 4, the canister 12 is substantially cylindrical in shape, having a blind first end 13, a second end 14 having a cooling coil port 24, and a lateral wall 15. The cooling coil port 24 is provided with a mounting flange 25 welded to the second end 14 of the canister 12. The canister 12 is also provided with a flanged inlet 16 and a flanged outlet 20. As depicted in FIGS. 3 and 4, the inlet 16 is located in the lateral wall 15 adjacent the first end 13 and the outlet 20 is located on the opposing side of the canister 12 adjacent the second end 14.

It will be understood that where several canisters are coupled in series, the inlet 16 of each successive canister 12 operationally will be located alternatively adjacent the first end 13 and the second end 14. The location of the inlet 16 and the outlet 20 adjacent opposing ends of the canister 12 and on opposing sides of the lateral wall 15 is preferred. This arrangement forces the process stream received into the canister 12 through the inlet 16 to circulate through the canister 12 and around and through the coil 30 before exiting through the outlet 20.

As shown in FIG. 4, and as will be discussed more fully below, the canister 12 is preferably provided with several probe ports 43, 44, and 45. An upper lateral probe port 43 and a lower lateral probe port 44 are advantageously situated near the midpoint of the lateral wall 15. An end probe port 45 may be advantageously provided in the blind end 13. In the preferred embodiment, the canister 12 is provided with upper and lower lateral probe ports 43 and 44 and an end probe port 45. This arrangement offers considerable flexibility in positioning a number of probes 50 in the canister to detect important simulation parameters such as corrosion rate and temperature. Although throughout the present discussion reference is made to probes 50 positioned within the probe ports 43, 44, 45, 46, it should be noted that corrosion coupons 56 may be preferred and can be readily positioned within any or all probe ports 43, 44, 45, 46 depending upon the particular corrosion data sought.

As can be seen in FIG. 4, the canister 12 is provided with lateral probe ports 43 and 44 and an end probe port 45. The probe ports 43, 44, 45 preferably include threaded weldolets 48 welded to and extending from the blind end 13 and the lateral wall 15 of the canister 12. Probes 50 may be removably positioned in the probe ports so as to penetrate into the canister 12. Such probes may be corrosion probes, temperature probes or combination corrosion and temperature probes as are well known in the art. One such corrosion probe is made by Rohrback Instruments and marketed under the trademark Corrosometer. Alternatively, the corrosion probe may be of the retractable coupon type, as is well known in the field of corrosion detection. Temperature probes will typically be of the thermocouple type. It is preferable to provide both corrosion and temperature probes, or combination probes in each canister 12 of the simulator 10 to collect data correlating corrosion activity to temperature.

In operation, condensation will occur in the canisters 12a, 12b, 12c, with most of the condensate accumulating in the canister where the process stream reaches the dew point. The location of the probe ports 43, 44, 45 as indicated above enables probes 50 to be positioned in both the vapor phase and the liquid phase. Probes 50 positioned in the upper lateral probe port 43 and the end probe port 45 will generally detect corrosion activity of the process stream in the vapor phase, whereas a probe positioned in the lower lateral probe port 44 may detect corrosion activity of the liquid condensate that accumulates in the canister 12. In addition, surface mounted corrosion coupons 54 may be positioned within some or all of the canisters 12 to measure either vapor phase corrosion activity, condensate corrosion activity, or both.

In addition, a probe port 46 may be provided in the coil flange 31 as shown in FIGS. 3 and 4. A probe 50 inserted in the coil flange probe port 46 will extend into the canister 12 when the coil is mounted onto the canister 12 as discussed below, and will be surrounded by the coil 30 as seen in FIG. 4. Alternatively, the coil flange 31 may be provided with a standard weight loss coupon 56 as illustrated in FIG. 5.

In the event no probe is positioned in a particular probe port, that port will generally be capped with a probe port cap 52 as shown in the case of the upper lateral probe port 43 in FIGS. 3 and 4. In certain applications it may be desirable to extract samples of condensate collecting in the canister 12. For this purpose a sampling assembly 90 may be coupled to the lower lateral probe port 44. As illustrated in FIG. 4, the sampling assembly 90 includes a reducing coupling 91 mounted onto the probe port 44 and a first ball valve 93 coupled to the reducing coupling 91 by means of a close nipple 92. A second ball valve 95 is in turn coupled in series with the first ball valve 93 by means of a close nipple 94. This arrangement permits a sample of the condensate to be captured between the ball valves by opening the first ball valve 93 with the second ball valve 95 in the closed position. The sample is then extracted by first shutting the first ball valve 93 and opening the second ball valve 95 to allow the sample to gravity drain into a suitable recipient (not shown). It is understood, of course, that other arrangements for extracting samples of the condensate can be employed satisfactorily.

The coil port 24 is preferably flanged. The canister mounting flange 25 is welded onto the end 14 of the canister 12 and includes mounting bolt holes 26. The coil assembly 28 includes a corresponding mounting flange 31 which mates with the canister flange 25 when the coil 30 is fully inserted into the canister 12. In the mounted position, bolt holes 32 (shown in FIG. 5) in the coil assembly mounting flange 31 line up with the corresponding holes 26 in the canister flange 25 and bolts 38 hold the coil assembly 28 securely in place on the canister 12 and assure a liquid and gas seal between the canister flange 25 and the coil assembly flange 31.

The inlet 16 and outlet 20 are preferably similarly flanged. In the case of the inlet 16 and outlet 20 however, pipe extensions 17 and 21 are welded to the lateral wall 15 of the canister 12 and serve to locate the inlet and outlet flanges 18 and 22 at a convenient distance from the lateral wall 15. This arrangement facilitates coupling several canisters 12a, 12b, 12c in series while allowing sufficient clearance between canisters for the coil mounting flanges 25, 31. The inlet and outlet flanges 18, 22 are provided with bolt holes 19 and 23 respectively for receiving mounting bolts (not shown) during installation of the canister 12 in a specific application and during coupling of several canisters 12a, 12b, 12c in series. The inlet and outlet flanges 18, 22 are machined to assure a sufficient gas seal when coupled to one another or to a source or discharge line.

As can be seen most clearly in FIG. 5, the coil assembly 28 includes a coil 30 having an inlet 34 and an outlet 36. In the preferred embodiment, the inlet 34 and outlet 36 of the coil 30 penetrate through the coil assembly flange 31 and are sealed to the flange, preferably by welding or soldering. Inlet and outlet fittings 35 and 37 respectively are provided for coupling the coil to a coolant source or discharge, or to the preceding or successive coil in a series of coils. The inlet and outlet fittings 35, 37 may be of any suitable type commonly used in industrial applications, and are preferably nut and ferrule or flare type fittings providing a good fluid seal when placed in service. As discussed above, a corrosion probe, or weight loss coupon 56 may be mounted on the coil assembly flange 31. It has been found that a coil flange mounted probe or weight loss coupon 56 as shown in FIG. 5 provides the additional benefit of balancing the flow of the process stream through the simulator where the position of the inlet 16 and the outlet 20 alternate due to series mounting and a probe is provided in the blind end 13 of the canisters 12a, 12b, 12c.

It should be noted that, as best illustrated in FIGS. 4 and 5, the coil assembly flange 31 and the coolant inlet 34 and outlet 36 are preferably symmetric about a horizontal axis, permitting the coil assembly 28 to be mounted in two different positions by simply inverting the entire assembly 28. This feature is particularly useful where a number of canisters 12a, 12b, 12c are mounted in series, as it allows each cooling coil assembly 28a, 28b, 28c to be positioned so that the process stream entering each canister contacts a cooling coil having a similar orientation. Maintaining a particular orientation of the cooling coils with respect to the incoming process stream is generally desired to obtain consistent corrosion data and a uniform countercurrent flow relation between the process stream and the coolant stream.

The simulator set forth in the foregoing description is specifically adapted for implementation of an improved method for simulating the corrosion activity of a process stream. In accordance with this method, a process stream is passed through a series of canisters as set forth hereinabove. Coolant is passed through a series of cooling coils in counterflow to the process stream. In the preferred arrangement for carrying out the improved simulation method, one cooling coil is positioned within each of the canisters in the series of canisters to cool the process stream. At least a portion of the process stream is condensed within the series of canisters, and the corrosion activity within the canisters is monitored.

We claim:

1. A corrosion simulator comprising:
    a plurality of modular canisters, each of said canisters having a process stream receiving inlet, a process stream discharge outlet, and at least one probe port, said plurality of canisters being interconnected in series, the inlet of a first canister in said series being coupled to a process stream source and the outlet of a last canister in said series being coupled to a process stream discharge point; and
    a plurality of cooling coils, one of said cooling coils being positioned within each of said canisters, each of said cooling coils having an inlet for receiving a coolant stream and an outlet for discharging said coolant stream, said cooling coils being interconnected in series, a first coil being positioned within said last canister and the inlet of said first coil in said series of coils being coupled to a source of coolant, and a last coil being positioned in said first canister and the outlet of said last coil in said series of coils being coupled to a coolant discharge point.

2. The apparatus as set forth in claim 1, further comprising at least one corrosion probe removably positioned within at least one of said canisters through said at least one probe port, wherein the probe part measures corrosive activity of said press stream.

3. The apparatus as set forth in claim 1, further comprising at least one corrosion probe removably positioned within at least one of said canisters through said at least one probe port, wherein the probe part measures corrosive activity of condensate in the process stream.

4. The apparatus as set forth in claim 1, further comprising at least one temperature probe removably positioned within at least one of said canisters through said at least one probe port, wherein the temperature probe measures temperature in the process stream.

5. The apparatus as set forth in claim 1, further comprising at least one corrosion coupon positioned within at least one of said canisters.

6. The apparatus as set forth in claim 1, further comprising a flow regulating valve coupled to said series of coils of said coolant stream through said cooling coils.

7. The apparatus as set forth in claim 1, wherein at least one of said canisters further comprises a condensate sampling port, and a condensate sampling valve coupled to said condensate sampling port.

8. A corrosion apparatus for simulating use in a process stream flowing through a process line, comprising:
    a plurality of modular canisters, each of said canisters having an inlet wherein the inlet is used for receiving a portion of said process stream, an outlet for use in discharging said portion of said process stream, a cooling coil port, and at least one probe port, said plurality of canisters being interconnected in series, the inlet of a first canister in said series being coupled to said process line wherein the inlet is used for diverting a portion of said process stream into said series of canisters and the outlet of a last canister in said series of canisters being coupled to a process stream discharge point such that a sufficient pressure drop is established across said canisters to assure movement of said portion of said process stream from said first canister through said last canister; and
    a plurality of cooling coils, one cooling coil being positioned within each of said canisters, and each of said cooling coils having a coolant receiving inlet and an outlet for use in discharging said coolant stream, said cooling coils being interconnected in series, a first coil in said series of coils being positioned in the last canister in said series of canisters and the inlet of said first coil being coupled to a source of coolant, and a last coil in said series of coils being positioned in the first canister in said series of canisters and the outlet of said last coil being coupled to a coolant discharge point such that a sufficient pressure drop is established across said coils to assure movement of coolant from said first coil through said last coil, counter to the flow of said process stream.

9. The apparatus as set forth in claim 8, further comprising a corrosion probe removably positioned within at least one of said canisters through said at least one probe port, wherein the probe port measures corrosive activity of said process stream.

10. The apparatus as set forth in claim 8, further comprising a corrosion probe removably positioned within at least one of said canisters through said at least one probe port, wherein the probe part measures corrosive activity of condensate in the process stream.

11. The apparatus as set forth in claim 8, further comprising at least one temperature probe removably positioned within at least one of said canisters through said at least one probe port wherein the temperature probe measures temperature in the process stream.

12. The apparatus as set forth in claim 8, further comprising at least one corrosion coupon positioned within at least one of said canisters.

13. The apparatus as set forth in claim 8, further comprising a flow regulating valve coupled to said series of cooling coils of said coolant stream through said cooling coils.

14. The apparatus as set forth in claim 8, wherein at least one of said canisters further comprises a condensate sampling port, and a condensate sampling valve coupled to said condensate sampling port.

* * * * *